(12) United States Patent
Asaad

(10) Patent No.: US 8,956,414 B2
(45) Date of Patent: Feb. 17, 2015

(54) INTERVERTEBRAL BODY IMPLANT, INSTRUMENT AND METHOD

(75) Inventor: Wagdy W. Asaad, Burr Ridge, IL (US)

(73) Assignee: SpineCraft, LLC, Westmont, IL (US)

( * ) Notice: Subject to any disclaimer, the term of this patent is extended or adjusted under 35 U.S.C. 154(b) by 591 days.

(21) Appl. No.: 12/764,614

(22) Filed: Apr. 21, 2010

(65) Prior Publication Data

US 2011/0264218 A1  Oct. 27, 2011

(51) Int. Cl.
| | | |
|---|---|---|
| A61B 17/58 | (2006.01) | |
| A61B 17/60 | (2006.01) | |
| A61F 2/00 | (2006.01) | |
| A61F 2/44 | (2006.01) | |
| A61F 2/46 | (2006.01) | |
| A61F 2/30 | (2006.01) | |
| A61F 2/28 | (2006.01) | |

(52) U.S. Cl.
CPC ............. *A61F 2/4465* (2013.01); *A61F 2/4611* (2013.01); *A61F 2/30942* (2013.01); *A61F 2002/2817* (2013.01); *A61F 2002/2835* (2013.01); *A61F 2002/3008* (2013.01); *A61F 2002/30538* (2013.01); *A61F 2002/30616* (2013.01); *A61F 2002/30779* (2013.01); *A61F 2002/30787* (2013.01); *A61F 2002/30879* (2013.01); *A61F 2002/30904* (2013.01); *A61F 2002/30957* (2013.01); *A61F 2002/30985* (2013.01); *A61F 2002/4475* (2013.01); *A61F 2002/4627* (2013.01); *A61F 2002/4628* (2013.01); *A61F 2310/00023* (2013.01); *A61F 2002/30507* (2013.01)
USPC .......................................... 623/17.16; 606/99

(58) Field of Classification Search
USPC ................................ 623/17.11–17.16; 606/99
See application file for complete search history.

(56) References Cited

U.S. PATENT DOCUMENTS

| | | |
|---|---|---|
| 6,648,915 B2 | 11/2003 | Sazy |
| 6,749,636 B2 | 6/2004 | Michelson |
| 6,890,355 B2 | 5/2005 | Michelson |
| 6,989,031 B2 | 1/2006 | Michelson |
| 7,018,413 B2 | 3/2006 | Kurger |
| 7,041,137 B2 | 5/2006 | Fulton |
| 7,204,853 B2 | 4/2007 | Gordon |
| 7,238,203 B2 | 7/2007 | Bagga et al. |
| 7,316,714 B2 | 1/2008 | Gordon et al. |

(Continued)

*Primary Examiner* — Andrew Yang
*Assistant Examiner* — Diana S Jones
(74) *Attorney, Agent, or Firm* — Law Office of Alan W. Cannon

(57) ABSTRACT

Interbody implant systems and methods of implant interbody implants are described. In one aspect, an implant includes a body have a distal end portion and a proximal end portion and a first articulation surface formed at a proximal end of the proximal end portion, An insertion instrument includes an elongate shaft having a proximal end portion and a distal end portion; and a second articulation surface formed at a distal end of the distal end portion. The second articulation surface is configured to interface with the first articulation surface. An attachment member is configured to connect the implant to the insertion instrument. The attachment member is actuatable to compress the first and second articulation surfaces together in a locked configuration with sufficient force to prevent relative rotation between the first and second articulation surfaces. The attachment member is actuatable to reduce an amount of compression force existing in the locked configuration to place the first and second articulation surfaces in an unlocked configuration such that the first articulation surface can rotate relative to the second articulation surface.

19 Claims, 11 Drawing Sheets

(56) References Cited

U.S. PATENT DOCUMENTS

| | | |
|---|---|---|
| 7,331,995 B2 | 2/2008 | Eisermann et al. |
| 7,364,589 B2 | 4/2008 | Eisermann |
| 7,427,294 B2 | 9/2008 | Thramann et al. |
| 7,435,262 B2 | 10/2008 | Michelson |
| 7,455,692 B2 | 11/2008 | Michelson |
| 7,503,934 B2 | 3/2009 | Eisermann et al. |
| 7,527,638 B2 | 5/2009 | Anderson et al. |
| 7,540,882 B2 | 6/2009 | Michelson |
| 7,547,318 B2 | 6/2009 | Birkmeyer et al. |
| 7,550,010 B2 | 6/2009 | Humphreys et al. |
| 7,556,851 B2 | 7/2009 | Humphreys et al. |
| 7,611,536 B2 | 11/2009 | Michelson |
| 7,618,454 B2 | 11/2009 | Bentley et al. |
| 7,635,389 B2 | 12/2009 | Yu et al. |
| 7,655,010 B2 | 2/2010 | Sherhan et al. |
| 2002/0055781 A1 | 5/2002 | Sazy |
| 2003/0083747 A1 | 5/2003 | Winterbottom et al. |
| 2003/0125739 A1 | 7/2003 | Bagga et al. |
| 2004/0010315 A1 | 1/2004 | Song |
| 2004/0143330 A1 | 7/2004 | Sazy |
| 2004/0158328 A1 | 8/2004 | Eisermann |
| 2004/0225365 A1 | 11/2004 | Eisermann et al. |
| 2004/0267366 A1 | 12/2004 | Kruger |
| 2005/0038511 A1 | 2/2005 | Martz et al. |
| 2005/0070900 A1 | 3/2005 | Serhan et al. |
| 2005/0075734 A1 | 4/2005 | Fulton et al. |
| 2005/0143819 A1 | 6/2005 | Falahee |
| 2005/0154461 A1 | 7/2005 | Hemphreys et al. |
| 2005/0154464 A1 | 7/2005 | Hemphreys et al. |
| 2005/0154466 A1 | 7/2005 | Hemphreys et al. |
| 2005/0171610 A1 | 8/2005 | Humphreys et al. |
| 2005/0209698 A1 | 9/2005 | Gordon et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283247 A1 | 12/2005 | Gordon et al. |
| 2005/0283248 A1 | 12/2005 | Gordon et al. |
| 2006/0129244 A1 | 6/2006 | Ensign |
| 2006/0136059 A1 | 6/2006 | Thramann |
| 2006/0142858 A1 | 6/2006 | Colleran et al. |
| 2006/0195192 A1 | 8/2006 | Gordon |
| 2006/0247775 A1* | 11/2006 | Thramann et al. ......... 623/17.11 |
| 2006/0287725 A1 | 12/2006 | Miller |
| 2007/0067035 A1 | 3/2007 | Falahee |
| 2007/0073406 A1 | 3/2007 | Gordon et al. |
| 2007/0129804 A1 | 6/2007 | Bentley et al. |
| 2007/0162138 A1 | 7/2007 | Heinz |
| 2007/0191945 A1 | 8/2007 | Yu et al. |
| 2007/0213826 A1* | 9/2007 | Smith et al. ................ 623/17.11 |
| 2007/0225808 A1 | 9/2007 | Warnick |
| 2007/0270956 A1 | 11/2007 | Heinz |
| 2007/0282449 A1 | 12/2007 | Villiers et al. |
| 2008/0051900 A1 | 2/2008 | Villiers et al. |
| 2008/0051901 A1 | 2/2008 | Villiers et al. |
| 2008/0077248 A1 | 3/2008 | Murillo et al. |
| 2008/0097610 A1 | 4/2008 | Guyer et al. |
| 2008/0154375 A1 | 6/2008 | Serhan et al. |
| 2008/0221586 A1 | 9/2008 | Garcia-Bengochea et al. |
| 2008/0221694 A1* | 9/2008 | Warnick et al. ............ 623/17.16 |
| 2008/0221695 A1 | 9/2008 | Jacofsky et al. |
| 2008/0249622 A1 | 10/2008 | Gray |
| 2008/0306557 A1 | 12/2008 | Altarac et al. |
| 2009/0043312 A1 | 2/2009 | Koulisis et al. |
| 2009/0093885 A1 | 4/2009 | Levieux et al. |
| 2009/0105833 A1 | 4/2009 | Hovda et al. |
| 2009/0143859 A1 | 6/2009 | McClellan, III et al. |
| 2009/0182428 A1 | 7/2009 | Mcclellan, III et al. |
| 2009/0216234 A1 | 8/2009 | Farr et al. |
| 2009/0234455 A1 | 9/2009 | Moskowitz et al. |
| 2009/0254183 A1 | 10/2009 | Humphreys et al. |
| 2009/0254184 A1 | 10/2009 | Humphreys et al. |
| 2009/0259255 A1 | 10/2009 | Humphreys et al. |
| 2009/0265007 A1 | 10/2009 | Colleran |
| 2009/0270986 A1 | 10/2009 | Christensen |
| 2009/0298776 A1 | 12/2009 | McKay |
| 2009/0298777 A1 | 12/2009 | McKay |
| 2009/0326658 A1 | 12/2009 | Allard |
| 2010/0004654 A1 | 1/2010 | Schmitz et al. |
| 2010/0016970 A1 | 1/2010 | Kapitan et al. |
| 2010/0016973 A1 | 1/2010 | Villiers et al. |
| 2010/0022824 A1 | 1/2010 | Cybulski et al. |

* cited by examiner

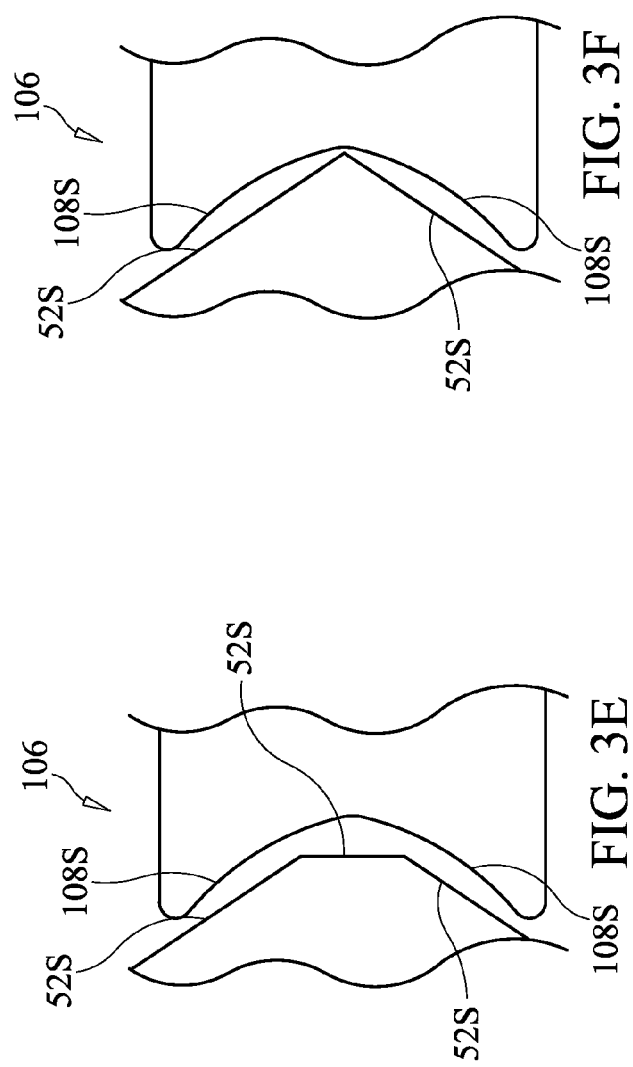
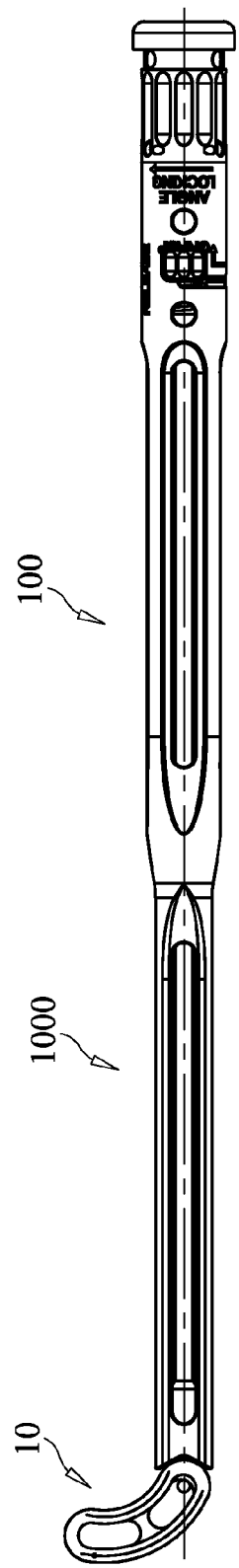
FIG. 3F
FIG. 3E
FIG. 4

INTERVERTEBRAL BODY IMPLANT, INSTRUMENT AND METHOD

BACKGROUND OF THE INVENTION

Back pain can be caused by a variety of factors, including, but not limited to the rupture or degeneration of one or more intervertebral discs due to degenerative disk disease, spondylolisthesis, deformative disorders, trauma, tumors and the like. In such causes, pain typically results from compression or irritation of spinal nerve roots by reduced spacing between adjacent vertebrae, a damaged disk and/or misalignment of the spine resulting of the injury or degeneration.

Common forms of treating such pain include various types of surgical procedures in which a damaged disk may be partially or totally excised, and one or more implants is inserted between adjacent vertebrae in an effort to restore the natural spacing and alignment between the vertebrae that existed previous to the injury or degeneration, so as to relieve the compression, irritation or pressure on the spinal nerve or nerves and thereby eliminate or significantly reduce the pain that the patient is experiencing. Typically, the one or more implants are used together with substances to encourage bone ingrowth to facilitate fusion between the adjacent vertebrae. Some procedures provide implants that allow at least some limited motion between the adjacent vertebrae, even after opposite ends of the implant are fixed to the adjacent vertebrae, respectively.

Among know procedures for performing fusion are PLIF (posterior lumbar interbody fusion), ALIF (anterior lumbar interbody fusion) and TLIF (transverse or transforaminal lumbar interbody fusion). A PLIF procedure achieves spinal fusion in the low back by inserting an implant such as a cage and, typically, graft material (to encourage bone ingrowth) directly into the disc space between adjacent vertebrae. The surgical approach for PLIF is from the back of the patient, posterior to the spinal column.

An ALIF procedure is similar to the PLIF procedure), except that in the ALIF procedure, the disc space is fused by approaching the spine through the abdomen, from an anterior approach, instead of through the lower back, from a posterior approach. Although previously there was a lot of interest in perfecting an endoscopic approach for ALIF surgery, it has largely been abandoned because it placed the great vessels (aorta and vena cava) at too great a risk.

A TLIF procedure involves a posterior and lateral approach to the disc space. To gain access to the disc space, the facet joint may be removed whereby access is gained via the nerve foramen. The TLIF procedure leaves more of the soft tissue intact compared to the PLIF procedure and is therefore less traumatic. Unlike the PLIF procedure, the TLIF procedure requires only minimal manipulation of neural tissues, thereby reducing the risk of nerve damage resultant from the fusion procedure. Typically only a single implant is placed in a TLIF procedure. The implant is inserted from a postero-lateral approach, as noted, and is ultimately placed in the middle-to-anterior aspect of the disc space.

In the typical ALIF, PLIF and TLIF procedures described, the adjacent vertebrae must be distracted apart by a substantial amount in order to allow the surgeon to advance the implant therebetween with relatively little resistance to the advancement of the implant along its delivery path. Also, the surgeon must typically release the implant at least once (generally more than once) as the implant is being delivered along the delivery path, since the implant is generally aligned posterior to anterior relative to the vertebrae, but is rotated along the course of the delivery path so that the orientation of the implant at the ultimate (target) position of implantation in the anterior aspect of the disc space, is generally transverse to the anterior-posterior direction. Thus, delivery of the implant generally requires temporary grasping or attachment of a delivery instrument and at least one iteration of releasing the grasp or attachment, repositioning the delivery instrument relative to the implant, reattaching or re-grasping the implant and further advancing the implant. This is not only cumbersome and extends the time to complete the procedure, but also runs the risk of displacing the implant from its current orientation and desired delivery path, which would result in malplacement of the implant and repositioning or even removal and re-insertion of the implant.

Still further, release and reattachment of an inserted to an implant is not always possible with currently existing TLIF implant/inserter designs. In such cases, the surgeon has to rely on various impactors to push and position the TLIF implant properly, and this can be difficult and therefore is sometimes not successful.

There is a continuing need for procedures that require less removal of tissues during the performance thereof. In this regard it would be desirable to provide implants and procedures that would require less removal f bone from the adjacent vertebrae than required by typical current procedures. It would further be desirable to provide implants and procedures that require less distraction of the adjacent vertebrae during placement of the implant. It would further be desirable to provide implants and instruments that do not require releasing and reattaching/re-grasping the implant during delivery of the implant. The present invention meets at least all of the above needs and desires.

SUMMARY OF THE INVENTION

According to one aspect of the present invention, an interbody implant system includes: an implant including a body have a distal end portion and a proximal end portion and a first articulation surface formed at a proximal end of the proximal end portion; and an insertion instrument including an elongate shaft having a proximal end portion and a distal end portion; a second articulation surface formed at a distal end of the distal end portion, the second articulation surface configured to interface with the first articulation surface; and an attachment member configured to connect the implant to the insertion instrument; wherein the attachment member is actuatable to compress the first and second articulation surfaces together in a locked configuration with sufficient force to prevent relative rotation between the first and second articulation surfaces, and the attachment member is actuatable to reduce an amount of compression force existing in the locked configuration to place the first and second articulation surfaces in an unlocked configuration such that the first articulation surface can rotate relative to the second articulation surface.

In at least one embodiment, the second articulation surface is substantially V-shaped.

In at least one embodiment, the first articulation surface comprises multiple, flat facets adjacent one another.

In at least one embodiment, the second articulation surface is substantially V-shaped having two contacting surfaces, wherein each of the contacting surfaces contacts one of the facets.

In at least one embodiment, one of the facets is located between the facets contacted by the contacting surfaces.

In at least one embodiment, the implant comprises an elongate opening, and the attachment member is configured and dimensioned to freely pass through the elongate opening in a first orientation relative to the elongate opening, but when in a second orientation relative to the elongate opening, the attachment member is prevented from passing through the elongate opening.

In at least one embodiment, a connection actuator is located on a proximal end portion of the elongate shaft, the connection actuator being actuatable to move the attachment member from the first orientation to the second orientation and from the second orientation to the first orientation.

In at least one embodiment, a compression actuator is located on the proximal end portion of the elongate shaft, the compression actuator being actuatable to move the attachment member in an axial direction relative to the elongate shaft along a longitudinal axis of the elongate shaft.

In at least one embodiment, the implant comprises first and second curved sides extending between the proximal and distal end portions and top and bottom surfaces formed between proximal and distal ends of the body, wherein the top and bottom surfaces each comprise an elongated tooth adjacent each side, extending generally along a direction of each respective side and protruding outwardly from the respective surface.

In another aspect of the present invention, an interbody implant is provided that includes: an implant including a body have a distal end portion and a proximal end portion and a first articulation surface formed at a proximal end of the proximal end portion; wherein the first articulation surface is configured and dimensioned to interface with a second articulation surface of an insertion instrument and the implant is configured and dimensioned to be connected to an attachment member of the insertion instrument, such that the attachment member is actuatable to compress the first and second articulation surfaces together in a locked configuration with sufficient force to prevent relative rotation between the first and second articulation surfaces, and the attachment member is actuatable to reduce an amount of compression force existing in the locked configuration to place the first and second articulation surfaces in an unlocked configuration such that that first articulation surface can rotate relative to the second articulation surface.

In at least one embodiment, the implant comprises an elongate opening configured and dimensioned to allow the attachment member, in a first orientation relative to the elongate opening, to freely pass through the elongate opening, and to prevent passage of the attachment member therethrough when the attachment member is in a second orientation relative to the elongate opening.

In at least one embodiment, the implant is unitary, the body is unitary and comprises first and second curved sides extending between the proximal and distal end portions and top and bottom surfaces bounded by the first and second sides and proximal and distal ends of the body.

In at least one embodiment, at least one elongated tooth is provided adjacent each side on each of the top and bottom surfaces, each elongated tooth extending generally along a direction of each respective side and protruding outwardly from the respective surface.

In at least one embodiment, at least one retropulsion resistor is formed in at least one elongated tooth, each retropulsion resistor being configured to permit advancement of the implant into an interbody space, but to prevent retropulsion of the implant out of the interbody space.

In at least one embodiment, at least one series of teeth are aligned along a curvature that generally conforms to a curvature of one of the sides.

In at least one embodiment, a series of retropulsion resistors are formed in an intermediate section of each of the teeth, respectively, each the series of retropulsion resistors being configured to permit advancement of the implant into an interbody space, but to prevent retropulsion of the implant out of the interbody space.

In another aspect of the present invention, an insertion instrument for inserting an interbody implant is provided, the instrument including: an elongate shaft having a proximal end portion and a distal end portion; an articulation surface formed at a distal end of the distal end portion, the articulation surface configured to interface with an interbody implant articulation surface; and an attachment member configured to connect an interbody implant to the insertion instrument; wherein the attachment member is actuatable to compress the articulation surface of the instrument and the interbody implant articulation surface together in a locked configuration with sufficient force to prevent relative rotation between the articulation surfaces, and the attachment member is actuatable to reduce an amount of compression force existing in the locked configuration to place the articulation surfaces in an unlocked configuration such that the interbody implant articulation surface can rotate relative to the articulation surface of the instrument.

In at least one embodiment, the articulation surface of the instrument is substantially V-shaped.

In at least one embodiment, a connection actuator is located on a proximal end portion of the elongate shaft, the connection actuator being actuatable to move the attachment member from the first orientation to the second orientation and from the second orientation to the first orientation.

In at least one embodiment, the attachment member comprises the shape of a hammer head.

In at least one embodiment, a compression actuator is located on the proximal end portion of the elongate shaft, the compression actuator being actuatable to move the attachment member in an axial direction relative to the elongate shaft along a longitudinal axis of the elongate shaft.

In another aspect of the present invention, a method of inserting an interbody implant is provided, the method including: attaching an interbody implant to an inserter instrument, wherein the interbody implant includes at least a pair of curved teeth on both top and bottom surfaces and extending adjacent curved sides of the implant in a direction from a distal end to a proximal end of the implant; aligning a distal end of the implant between two bony surfaces; driving the implant, using the instrument, wherein the teeth of the implant cut tracks into the bony surfaces, respectively, and wherein curvature of the curved teeth establish the tracks and curved tracks and cause the implant to follow a curved insertion path; and at least one intermediate position between a starting insertion position of the implant and a final insertion position of the implant, providing sufficiently low compression force between an articulation surface of the implant and an articulation surface of the insertion instrument to allow rotation of the insertion instrument relative to the implant, while the insertion instrument remains connected to the implant.

In at least one embodiment, the sufficiently low compression force is provided during an entire extent of the insertion process by the insertion instrument.

In at least one embodiment, over a least a portion of the driving, rotation of the instrument relative to the implant is not allowed, the compression force between the articulation forces being increased to prevent relative rotation of the articulation surfaces.

In at least one embodiment, relative rotation between the instrument and the implant occurs more than once during insertion of the implant.

In at least one embodiment, the method includes detaching the instrument from the implant and further inserting the implant to the final position using an impactor instrument.

In at least one embodiment, retropulsion of the implant is prevented by at least one retropulsion resistor formed in at least one tooth of the implant.

These and other features of the invention will become apparent to those persons skilled in the art upon reading the details of the systems, implants, instruments and methods as more fully described below.

BRIEF DESCRIPTION OF THE DRAWINGS

FIG. 3E shows an arrangement of facets engaging contact surfaces according to an embodiment of the present invention.

FIG. 3F shows an arrangement of facets engaging contact surfaces according to another embodiment of the present invention.

FIG. 4 shows a system including an instrument and an implant, with the instrument attached to the implant in one of a plurality of orientations that can be established between the instrument relative to the implant according to an embodiment of the present invention.

DETAILED DESCRIPTION OF THE INVENTION

Figure 1B:
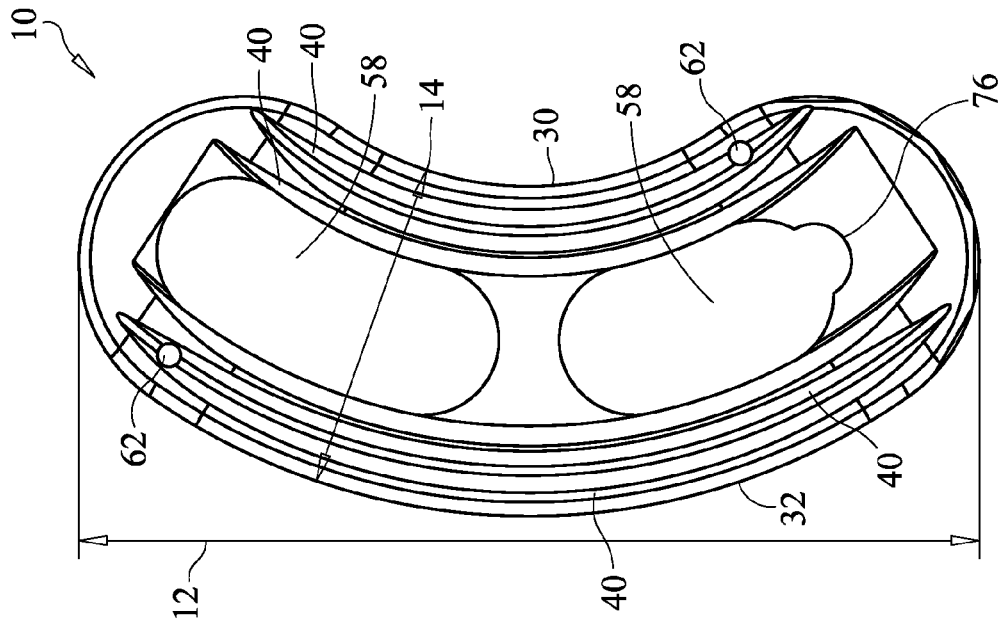
FIGS. 1A-1D show a perspective view, a top view, a side view and a proximal end view, respectively, of an implant according to an embodiment of the present invention.

Before the present systems, implants, instruments and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a tooth" includes a plurality of such teeth and reference to "the surface" includes reference to one or more surfaces and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

A "tooth" as defined herein, refers to a ridge formed in, or preferably extending out from a surface of the implant. The ridge may be either continuous, or is interrupted along an intermediate portion thereof by multiple retropulsion resistors. Retropulsion resistors may be sharp peaks of asymmetrical faces or base angles, forming a "shark-fins" like pattern when viewed laterally. The sharp peaks may be equally spaced from one another along the intermediate portion.

A "retropulsion resistor" is a feature configured to resist backing out of the implant once it has been finally placed, as well as at any location along its delivery pathway. One or more repulsion resistors may be formed in or on an implant, preferably in or on one or more teeth.

Figure 1A:
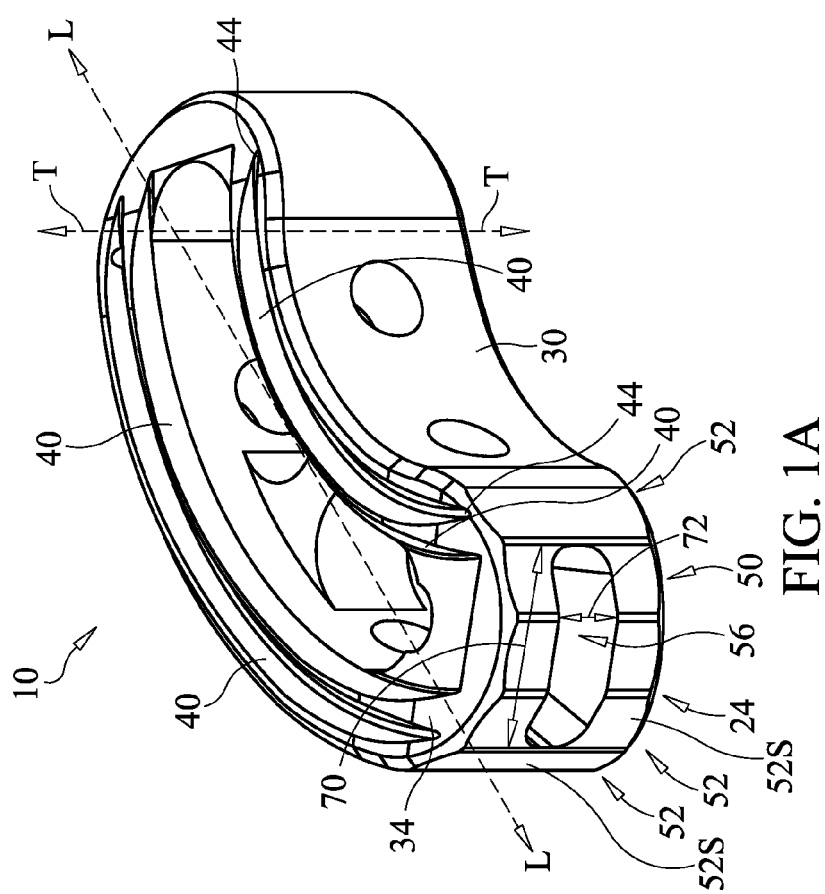
Figure 1D:
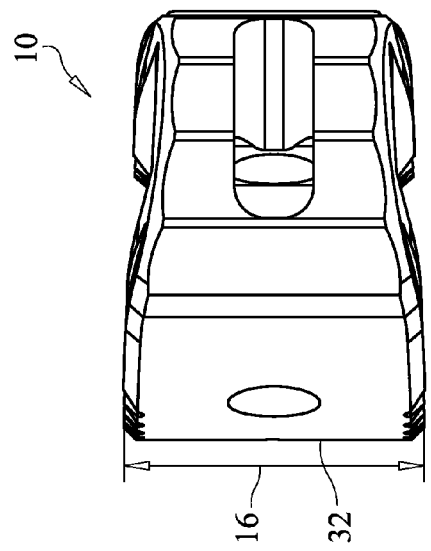
Figure 1E:
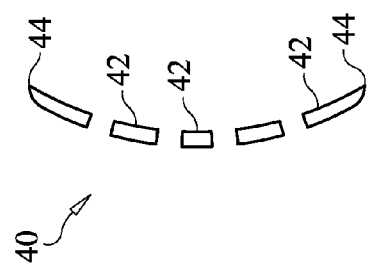
FIG. 1E illustrates an alternative embodiment of a tooth according to an embodiment of the present invention.
Figure 1C:
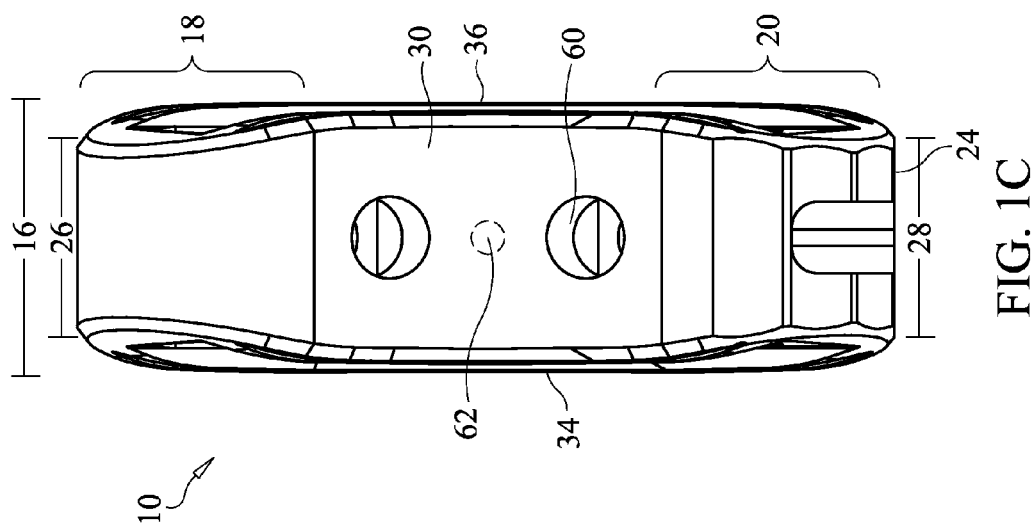

Referring now to the drawings in detail, FIGS. 1A-1D show a perspective view, a top view, a side view and a proximal end view, respectively, of an implant 10 according to an embodiment of the present invention. FIG. 1C is a right side view of the implant 10 in the orientation shown in FIG. 1B. Implant 10 is formed of a unitary body having a length 12 (see FIG. 1B), width 14 and height 16 (see FIG. 1C). The height 16 (see FIGS. 1C and 1D) is substantially constant over the length 12 and width 14, but tapers to form portions having less height at both end portions 18, 20, so that at least the distal end 22 and/or proximal end 24 has a height 26, 28, respectively (where 26 and 28 may be equal or unequal) less than height 16, as shown in FIG. 1C. The reduced height 26 of the distal end 22 and tapered, varying height of the distal end portion 18 facilitate insertion of the implant 10 between adjacent vertebral bodies. The reduced height 28 of the proximal end 24 and tapered, varying height of the proximal end portion 28 better conform this portion to the shape/contours of the inter-vertebral disk space for improve load sharing, that is with a more even load distribution over the length of the implant. Implants 10 can be manufactured to have a variety of sizes to accommodate different sizes of patients and different inter-vertebral locations. In one non-limiting example, implants 10 may be manufactured in lengths 10 of 28 mm, 30 mm, 32 mm and 23 mm and in 1 mm height 16 increments from 7 mm to 15 mm. The width 14 may be about 10 mm or about 11 mm, although this may also vary.

The sides 30, 32 of implant 10 are curved to generally follow the contour of the anterior wall of the intervertebral disc space. The top and bottom surfaces 34, 36 both have at least one tooth 40 adjacent each side 30, 32 that generally follows the curvature of the side that it is adjacent to. FIGS. 1A and 1B show two teeth 40 per side, giving a total of four teeth on the top surface 34 and four teeth on the bottom surface 36. It is noted that the present invention is not limited to four teeth 40 on each of the top and bottom surfaces 34, 36, as each surface 34, 36 may have two teeth 40 (one per side), three, five or six or more. It is further noted that, although teeth 40 are illustrated as having continuous lengths that protrude outwardly from the surfaces 34, 36, that teeth 40 need not be continuously formed. FIG. 1E illustrates an alternative embodiment in which tooth 40 is formed of discontinuous segments 42 which are aligned so as to follow the curvature of a side 30 or 32 of the implant 10. Although continuity is not required, each end of a tooth 40 (whether tooth 40 is continuous or discontinuous) is sharp, and preferably has a sharp edge 44 or point to facilitate cutting into the bone of one of the adjacent vertebrae, in a manner described in greater detail below. Likewise the tooth 40 or tooth segments 42 are provided with a cutting ridge 46 (see FIG. 7) along the top (or bottom, i.e., the portion that extends furthest from the top or bottom surface) to facilitate cutting through bone.

The proximal end 24 of implant 10 includes an articulation surface 50 configured and dimensioned for interfacing with an articulation surface of an insertion instrument 100 described in more detail below. As illustrated in FIG. 1A, articulation surface 50 includes five facets 52 located adjacent one another. However, the number of facets may vary from as little as three to a number greater than five. For example, for implants 10 made of PEEK, these implants may have as many as seven facets. Implants 10 made of metal such as titanium may have as many as fifteen facets. Facets 52 each have a substantially planar surface 52S aligned with the transverse axis T-T of implant 10, but wherein each surface 52S is angled relative to the surface 52S or pair of surfaces 52S that is/are adjacent to it.

The proximal end 24 is additionally provided with an elongate opening 56 configured and dimensioned to allow attachment and detachment of the instrument 100 to and from the implant 10.

Implant 10 is formed as a cage having a unitary body, with openings provided through the top and bottom surfaces 34, 36 to form cavities 58, wherein openings from the top surface are in communication with openings from the bottom surface and are configured and dimensioned to receive graft material, such as bone particles or chips, demineralized bone matrix (DBM), paste, bone morphogenetic protein (BMP) substrates or any other bond graft expanders, or other substances designed to encourage bone ingrowth into the cavities 58 to facilitate the fusion. Additionally the implant 10 may be provided with side openings 60 as shown that are also in communication with the cavities 58.

Implant 10 is preferably made from PEEK (polyetheretherketone) and is preferably machined therefrom, but alternatively, may be manufactured by injection molding or three-dimensional lithographic printing, for example. When manufactured by three-dimensional lithographic printing, implant 10 may be made of polymers, such as PEEK or other polymer and/or absorbable materials such as tri-calcium phosphate (TCP), hydroxyapatite (HA) or the like. When made of metal, implant 10 may be machined or made by metal powder deposition, for example. Alternatively, implant 10 may be made of PEKK (poly(oxy-p-phenyleneisophthaloyl-phenylene/oxy-p-phenyleneterephthaloyl-p-phenylene) or carbon-filled PEEK. Manufacturing the implant from any of these materials make it radiolucent, so that radiographic visualization can be used to view through the implant 10 to track the post-procedural results and progress of the fusion over time. Alternatively, implant 10 could be made of titanium or other biocompatible, radiopaque metal. However, this is less preferred as this type of implant would obscure post-procedural radiographic monitoring.

In order to facilitate visualization of the implant 10 during the procedure, so as to confirm that the implant is being delivered along a desirable delivery pathway and that the implant 10 is maintaining a desirable orientation, implant 10 is provided with at least three radiopaque markers 62. In the example shown, one marker 62 is provided adjacent side 32 at or near the top surface 34 of the distal end portion (FIG. 1B), a second marker 62 is provided adjacent side 30 at or near the bottom surface 36 of the proximal end portion (FIG. 1B), and a third marker 62 is provided somewhere between the first and second markers along the height, width and length dimensions of the implant (FIG. 1C). By placing radiopaque markers 62 as described, this enables radiographic viewing of the markers 62, at any location along the delivery pathway and during the procedure, as well as post-procedurally, to accurately determine the three-dimensional positioning of the implant 10. Thus, not only can the radiographic imaging determine the location that the implant 10 is placed in, it can also determine the three-dimensional orientation of the implant relative to the anatomy at the location that it is placed in.

Figure 2B:
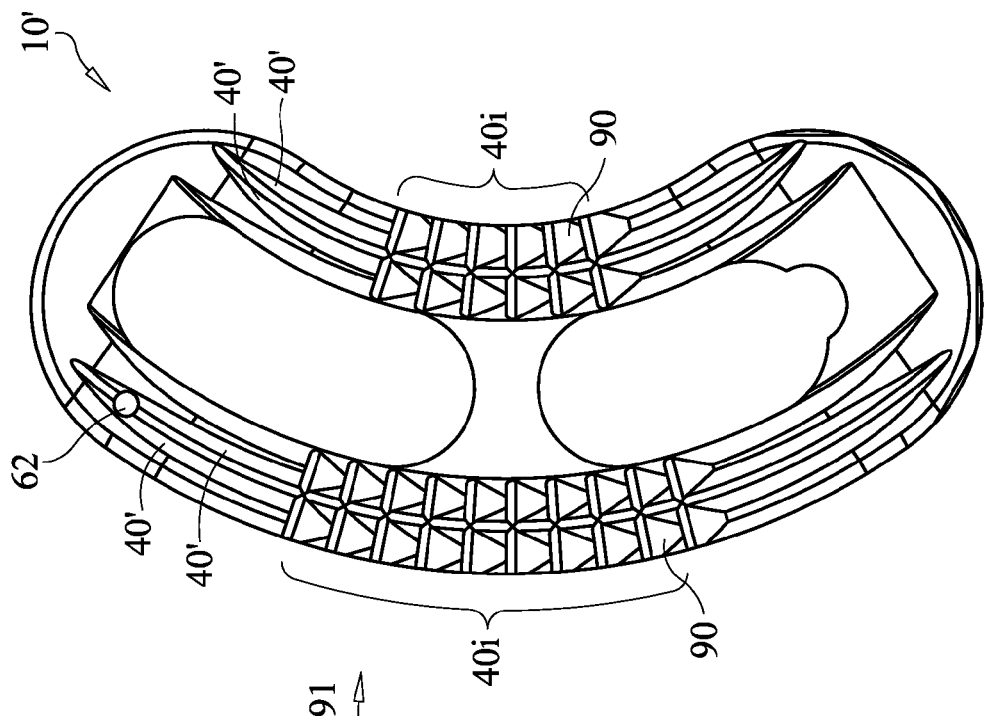
FIGS. 2A-2C show a perspective view, a top view, a side view, respectively, of an implant according to a presently preferred embodiment of the present invention.
Figure 2A:
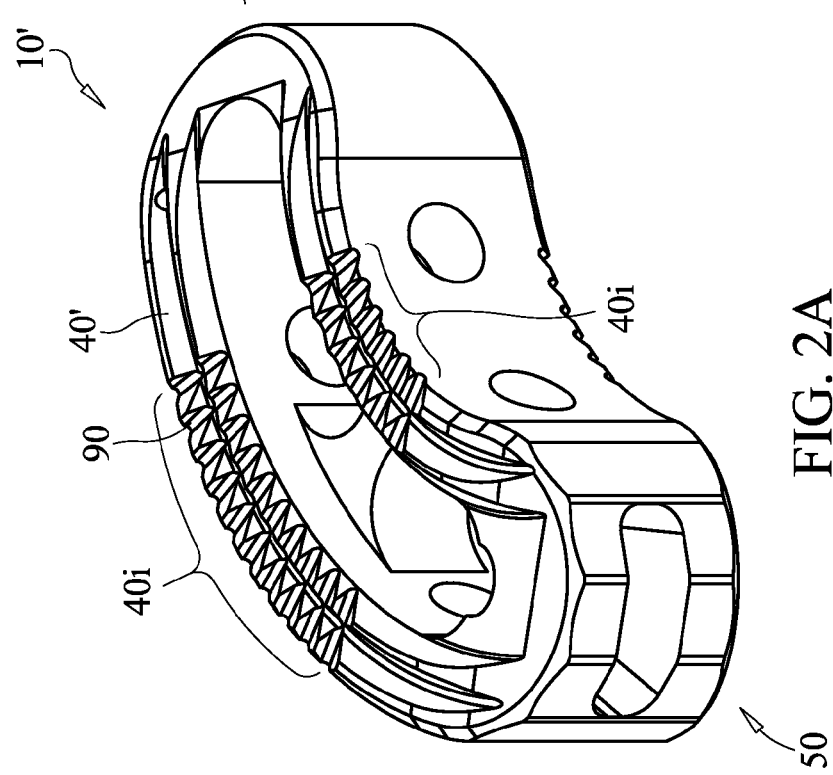
Figure 2D:
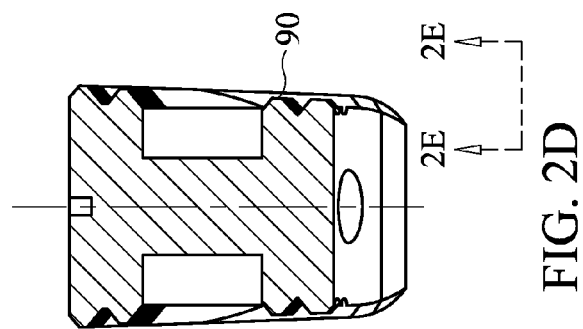
FIG. 2D is a cross-sectional view of the implant of FIG. 2C taken along line 2D-2D.
Figure 2E:
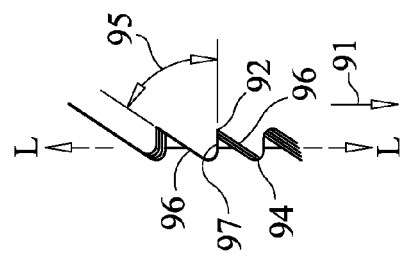
FIG. 2E is an enlarged detailed view of a portion of the sectional view of FIG. 2D indicated by line 2E-2E.
Figure 2C:
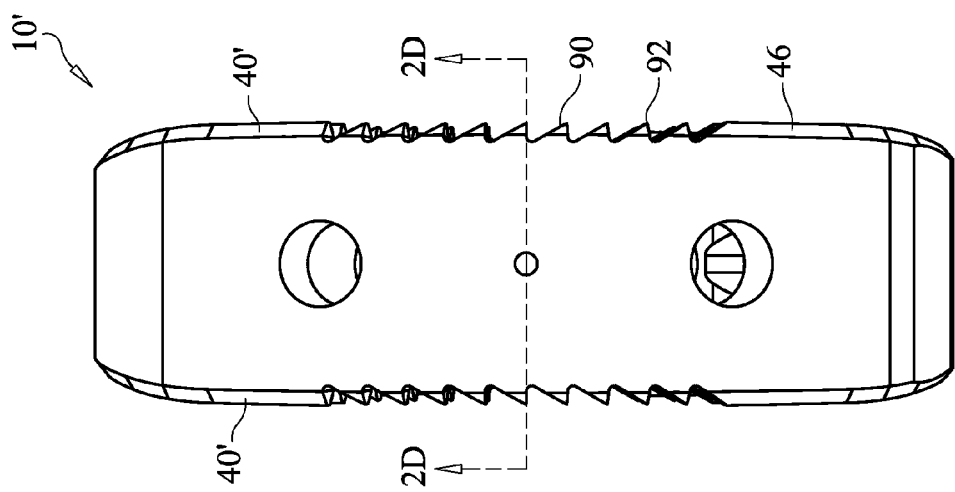

FIGS. 2A-2C show a perspective view, a top view and a side view, respectively, of an implant 10' according to a presently preferred embodiment of the present invention. Implant 10' is substantially the same as implant 10 except for the provision of retropulsion resistors 90 in the implant 10'. Accordingly, the same reference numerals have been used to components that are also present and substantially the same in implant 10.

Teeth 40' are provided that are substantially the same as teeth 40 at proximal and distal end portions thereof. However, retropulsion resistors 90 are formed in the intermediate portions 40i of the teeth 40'. Retropulsion resistors 90 include tips 92 that are substantially aligned with the cutting ridge 46 of the respective tooth 40' to facilitate cutting a channel into the bone as the implant 10' is inserted, being driven in a distal or curvilinear distal direction as indicated by arrow 91 in FIG. 2A. Retropulsion resistors 92 angle outwardly over a direction from a most inset portion (referred to as a valley) 94 toward tip or peak 92, as illustrated in FIGS. 2C-2E. On the opposite side 96 of the peak, the retropulsion resistor extends nearly perpendicular to the longitudinal axis L-L, as shown in FIG. 2E. The angle 95 thus formed between angled side 96 and perpendicular/transverse side 97 is about forty-five degrees to about 75 degrees, typically about sixty degrees.

Figure 7:
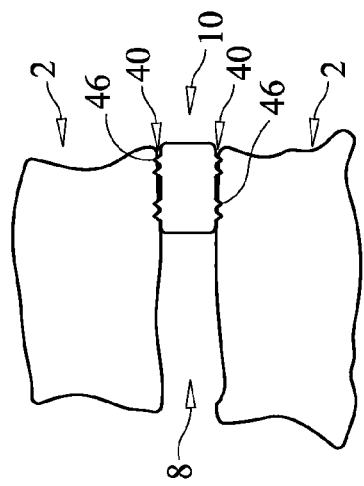
FIG. 7 illustrates a posterior view of vertebral bodies 2 at the start of the insertion of an implant 10 therebetween.

As formed, the retropulsion resistors assist in cutting the channels as the implant 10' is inserted between vertebrae in a manner as shown and described with regard to FIGS. 7-8. Tips 92 cut into the bone when moving in a substantially distal direction, but do not substantially resist, as the angled sides 96 are configured to slip in that direction of travel. If movement of the implant 10' is attempted in a substantially proximal direction however, tips 92 bite into the bone and the cut bone is guided against the substantially transverse side 97 which acts as an anchor or brake that prevents the backing out or substantial proximal movement of the implant 10'. Accordingly, once implant 10' has been placed between adjacent vertebrae to the extent where at least some of the retropulsion resistors have been placed between adjacent bone surfaces, the vertebrae will need to be further distracted to allow the implant 10' to be backed out of its current position.

As shown in FIGS. 2A-2E, the implant 10' preferably includes a plurality of adjacent retropulsion resistors 90 along each tooth 40' in an intermediate portion 40i thereof. However, the present invention is not so limited, since alternatively, one or more teeth 40 may be provided without any retropulsion resistors 90 as already noted above. Further, one or more teeth may be provided with only one retropulsion resistor 90. Various other combinations can also be used.

Figure 3A:
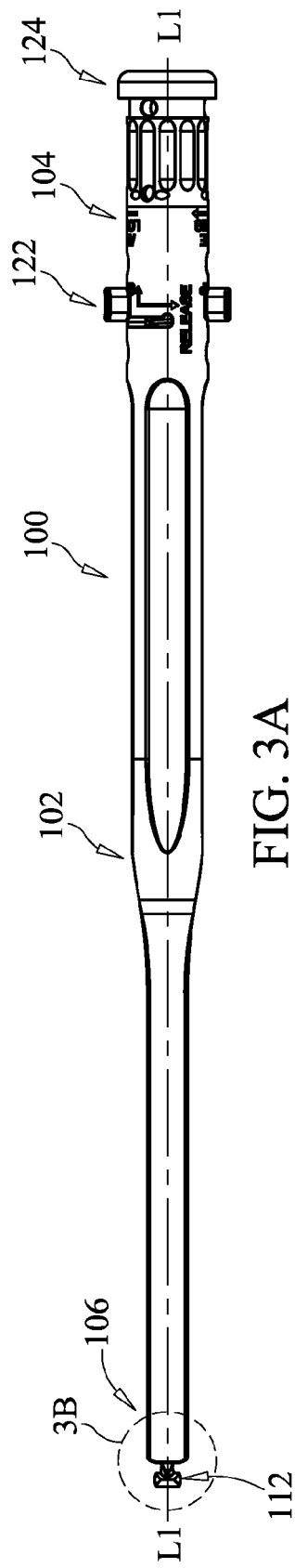
FIG. 3A shows a plan view of an insertion instrument configured and dimensioned for inserting an implant between adjacent vertebral bodies according to an embodiment of the present invention.
Figure 3B:
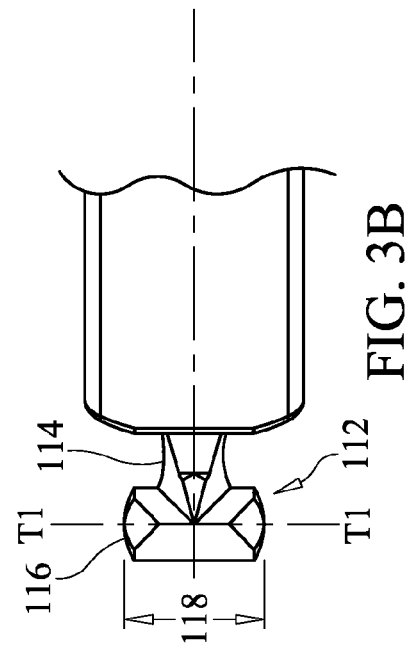
FIG. 3B is an enlarged, partial view of FIG. 3A taken within circle 3B.
Figure 3C:
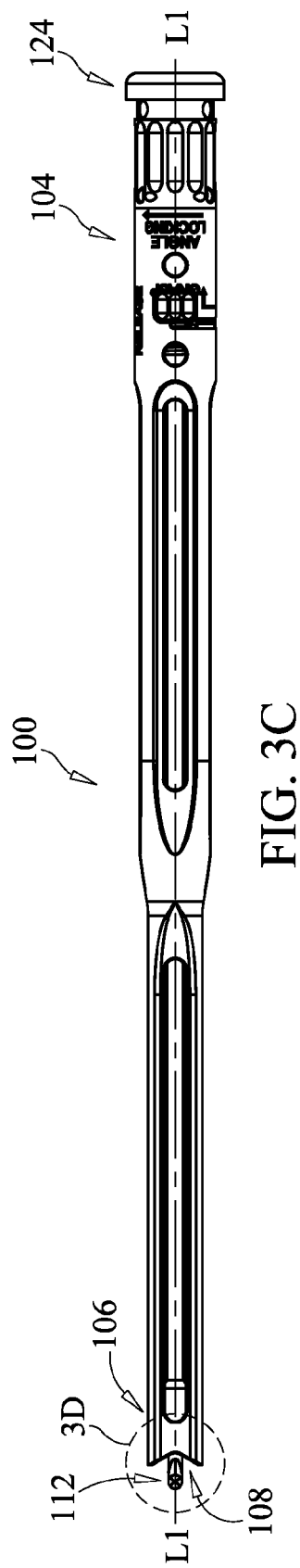
FIG. 3C shows another plan view of the insertion instrument of FIG. 1, after rotating the instrument about its longitudinal axis L1-L1 by ninety degrees.
Figure 3D:
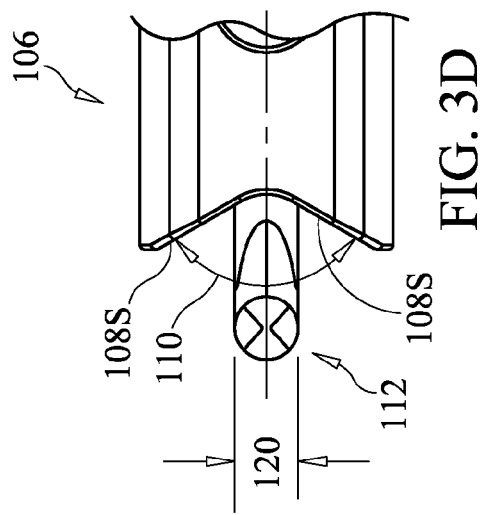
FIG. 3D is an enlarged, partial view of FIG. 3C taken within circle 3D.

FIG. 3A shows a plan view of an insertion instrument 100 configured and dimensioned for inserting implant 10 between adjacent vertebral bodies. Instrument 100 includes an elongate shaft 102 having a proximal end portion 104 and a distal end portion 106. FIG. 3C shows another plan view of the insertion instrument 100 shown in FIG. 3A, after rotating the instrument 100 about its longitudinal axis L1-L1 by ninety degrees. In the orientation of FIG. 3C, an articulation surface 108 is visible. Articulation surface 108 is configured and dimensioned to interface with the articulation surface 50 of implant 10. Articulating surface 108 is formed of a plurality of contact surfaces (preferably substantially planar surfaces) 108S that are angled relative to one another to substantially match the angulation between facet surfaces 52S. In the embodiment shown FIG. 3C, the articulating surface 108 is formed by two contact surfaces 108S (see also the enlarged, partial view in FIG. 3D) and is substantially V-shaped, although articulating surface 108 may alternatively be formed with more than two contact surfaces 108S. As shown in FIGS. 3C-3D, the angulation 100 between contact surfaces 108S is about 120 degrees. However, the amount of angulation 100 may vary to match facets 52 that vary by different amounts of angulation in alternative embodiments.

In a preferred embodiment, articulating surface 108 is configured and dimensioned so that the two contact surfaces 108S contact two facets 52 of implant 10 and so that a third facet 52 is interposed between the facets 52 that are contacted by contact surfaces 108S as illustrated in FIG. 3E. Alternatively, the articulating surface 108 and facets 52 may be configured and dimensioned so that contact surfaces 108S contact two immediately adjacent facets 52 as illustrated in FIG. 3F.

An attachment member 112 extends distally from the articulating surface 108 of instrument 100. Attachment member 112 is configured to attach implant 10 to the insertion instrument 100. In this regard, attachment member 112 has a neck portion 114 (see the enlarged detailed partial view of FIG. 3B) that is dimensioned to readily pass through opening 56 of implant 10 regardless of which orientation that the head 116 is in relative to contact surfaces 108S. That is, all cross-sectional dimensions of neck 114 are smaller than the height dimension of opening 56. On the other hand, head 116 which is attached to or integral with the distal end of neck 114, has a width 118 (see FIG. 3B) that is less that the width 70 (FIG. 1A) of opening 56 and has a height 120 (see FIG. 2D) that is less than the height 72 (FIG. 1A) of opening 56. However, width 118 is greater than height 72. Accordingly, in a release orientation, when the transverse axis T1-T1 of head 116 intersects with the planes that contact surfaces are substantially formed in, head 116 can be inserted into or removed from the implant 10 through opening 56.

Attachment member is mechanically connected through an actuation mechanism (not shown) to be driven by connection actuator 122 from the released orientation to an attached orientation and vice versa. Upon operating connection actuator 122, attachment member 112 is rotated by ninety degrees in a first rotational direction about longitudinal axis L1-L1 or in a second rotation direction (counter to the first rotational direction), depending upon the orientation that the attachment member is currently in. As shown connection actuator 122 comprises spring loaded push buttons that can be pressed inwardly and temporarily locked along an L-shaped slotted locking feature formed in the elongate shaft, to rotate the head 116 to the released orientation or configuration. By manipulating the push buttons along the L-shaped pattern, buttons 122 can be released to the configuration shown in FIG. 3A, whereby head 116 is rotated to the attached configuration shown in FIGS. 3A-3D. Thus, when the head 116 is in the attached configuration, the transverse axis T1-T1 aligns with the planes along which the contact surfaces 108S are substantially formed, as illustrated in FIG. 3D.

In a preferred embodiment shown, attachment member 112 is in the shape of a hammer, with neck 114 shaped like a hammer neck or handle and head 112 shaped like a hammer head. However, it is noted that other shapes of attachment members may be substituted, so long as they are configured and dimensioned to perform in the manners described with regard to attachment member 112.

The attachment member 112 is further mechanically connected to a compression actuator 124. Compression actuator is configured to be rotated about the longitudinal axis L1-L1 of instrument 100 relative to elongate shaft 102 to vary the distance between head 116 and articulating surface 108. Thus, when actuator 124 is rotated in one direction head 116 is drawn closer to articulating surface 108. Conversely, when actuator 124 is rotated in the counter direction, the head 116 is driven further away from articulating surface 108.

To attach the instrument 100 to device 10, the attachment member is positioned in the released orientation in a manner as described above, and head 116 is positioned (using compression actuator 124 if needed) so that a sufficient gap exists between the head 116 and the surfaces 108S to allow the head 116 to completely pass through the opening 56 while in the released orientation. Head 116 is then passed through the opening 56, and then rotated by ninety degrees, using connection actuator 122 to place head 116 in the attached orientation shown in FIGS. 3A-3D and so as to engage in receptacle 76 (see FIG. 1B). Receptacle 76 is configured and dimensioned to receive a curved surface of head 116, to thereby allow head 116 to rotate about its transverse axis T1-T1 relative to receptacle 76, but to prevent head 116 from translating back out of the opening 56, thereby securing the attachment. Receptacle may be substantially semi-circular from the top view and forms a bearing surface against which head 116 can rotate, unless sufficient compression has been established to prevent such rotation. Compression actuator 124 can then be rotated to draw the facets 52 into contact with surfaces 108S, either loosely to allow repositioning of the facets 52 relative to the contact surfaces 108S, or with sufficient compression to lock particular facets 52 into contact with the contact surfaces 108S and prevent repositioning of the facets 52 relative to the contact surfaces.

Release of the instrument is performed by essentially reversing the above steps. The compression actuator is counter-rotated to extend the head 116 by a sufficient distance so that it can be rotated to the released orientation, the connection actuator is operated in the opposite direction to counter-rotate head 116 by ninety degrees back to the released orientation, and then the operator can pull the head 116 out through the opening 56, thereby detaching instrument 100 from implant 10.

FIG. 4 shows a system 1000 including instrument 100 and implant 10, with instrument 100 attached to implant 10 in one of a plurality of orientations that can be established between the instrument 100 relative to the implant 10.

Figure 5:
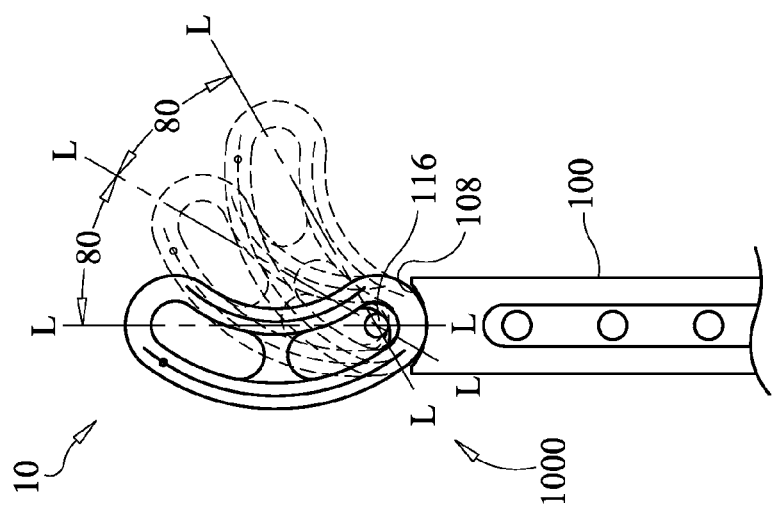
FIG. 5 illustrates a preferred embodiment of a system that allows positioning of the instrument in three different orientations relative to the implant according to an embodiment of the present invention.

FIG. 5 illustrates a preferred embodiment of system 1000 that allows positioning of instrument 100 in three different orientations relative to implant 10. In this embodiment, the amount of rotation of the implant relative to each adjacent position is measured by an angle 80 of about thirty degrees, measured by the longitudinal axis L-L of the implant 10 at each location.

As noted above, compression actuator 124 can be operated to draw facets 52 against contact surfaces 108S with sufficient compression force to prevent any change in orientation of instrument 100 relative to implant 10. Thus, relative rotation between implant 10 and instrument 100 is prevented in this locked configuration. Compression actuator can also be operated to reduce or release the compression force to an unlocked configuration, making it possible to reposition the orientation of the instrument 100 relative to the implant 10 without the need to disconnect or detach the instrument 100 from the implant, as the articulation surface 50 can rotate relative to the articulation surface 108. Once the instrument 100 has been repositioned to the next desired orientation, compression actuator 124 can again be operated to place the system 1000 back into the locked configuration, if desired.

Figure 6:
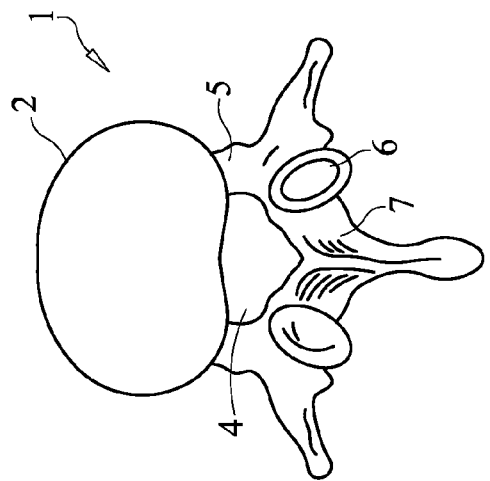
FIG. 6 illustrates a top view of a vertebra.

FIG. 6 illustrates a top view of a vertebra 1. The vertebral body 2 forms an anterior portion of the vertebra 1, and it is between adjacent ones of these vertebral bodies 2 (of adjacent vertebrae 1) that the interbody implant 10 of the present invention can be inserted in the performance of a fusion procedure. The spinal canal 3 is posterior to the vertebral body and is where the spinal cord passes through. Other bony features surround the spinal canal 3 both laterally and posterior to protect the spinal cord as well as to provide articulation joints to facilitate movement of the spine. Examples of such features are indicated as the pedicle 5, facet 6 and lamina 7.

FIG. 7 illustrates a posterior view of vertebral bodies 2 at the start of the insertion of an implant 10 therebetween. The structures posterior to the vertebral bodies 2 have not been shown to provide better clarity showing the interaction between the implant 10 and the vertebral bodies 2. As alluded to previously, the teeth 40 are sufficiently hard and sharp to cut into the bone of the respective vertebral bodies 2 to create tracks in the bone along which the implant can be advanced. Accordingly, the vertebral bodies do not need to be distracted apart by as great a distance as required in current procedures. The vertebral bodies need only be spaced apart by a distance slightly less than the height 16 of the implant 10, and preferably slightly greater than height 26 of the tapered distal end. This distance will vary, dependent upon each patient's pathology. However, in each case, the distraction is less than required for implanting prior art implants and this is advantageous, as less distraction of the nerves occurs since distraction of the adjacent vertebrae is less, This results in comparatively less irritation of the nerves and substantially less post-operative pain.

The curvature of the teeth 40 assists in delivering the implant along a curved delivery path, where the longitudinal axis L-L of the implant 10 is substantially aligned in a posterior-anterior direction relative to the patient/vertebrae 1 upon initial insertion of implant 10 into the disc space 8, and wherein the implant rotates substantially ninety degree about its transverse axis T-T from the starting position to the ultimate implantation position (target position), so that the longitudinal axis is transverse to posterior-anterior direction and preferably substantially normal to the posterior-anterior direction.

Figure 8A:
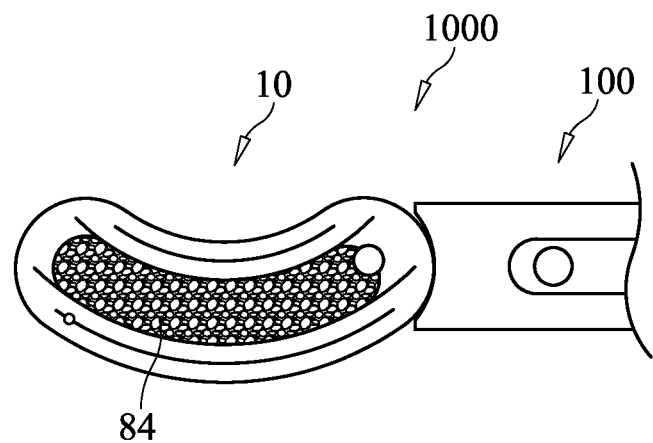
FIGS. 8A-8E illustrate a method (with an optional step shown in FIG. 8F) of inserting an interbody implant between adjacent vertebrae according to an embodiment of the present invention.

FIGS. 8A-8E illustrate a method (with an optional step shown in FIG. 8F) of inserting an interbody implant between adjacent vertebrae according to an embodiment of the present invention. FIG. 8A illustrates system 1000 in which implant 10 has been attached to inserter instrument 100, with implant 10 and instrument 100 relatively positioned in an initial configuration in which implant 10 is most nearly axially aligned (via longitudinal axis L-L) with the longitudinal axis L1-L1 of instrument 100. Note that the cavities 58 of implant 10 have also been packed with a bone ingrowth material, such as autologous bone, or other as noted above. When using autologous bone, the autologous bone can be harvested from the iliac crest of the patient, for example. Although this packing can be performed prior to attaching the implant 10 to the instrument 100 it is preferably done after the implant 10 has been securely attached to the instrument 100.

Figure 8B:
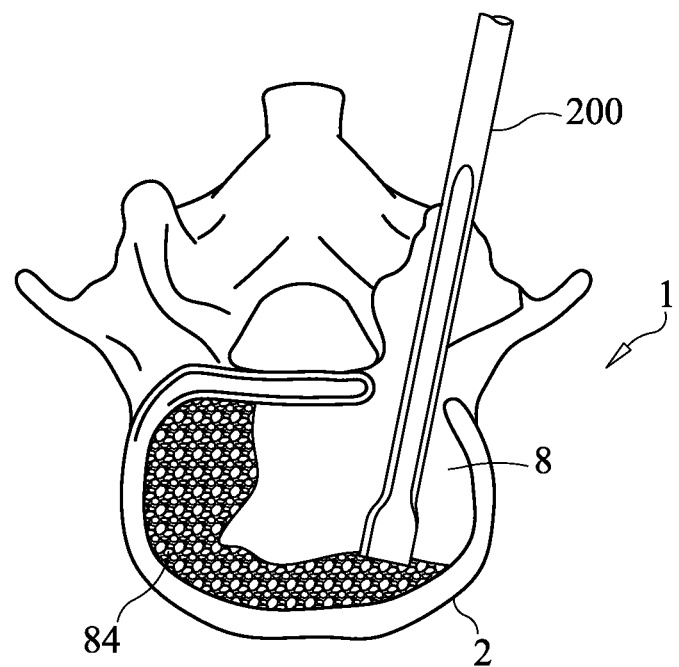
Figure 8C:
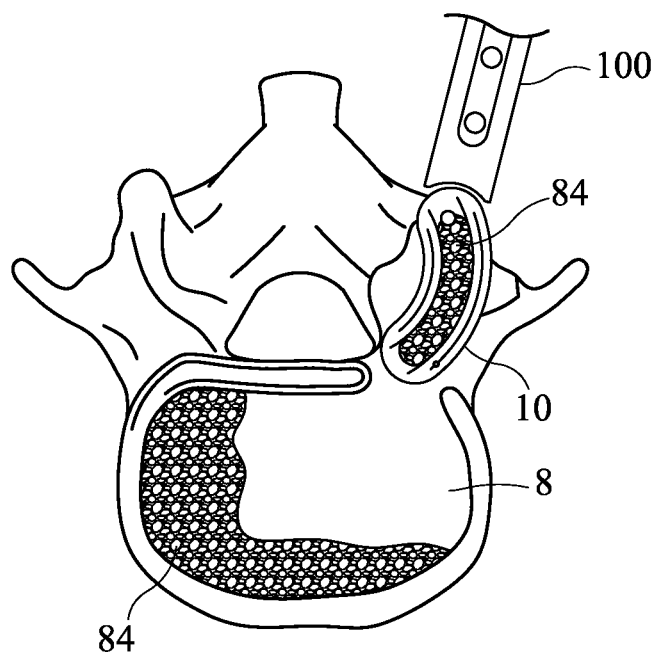

FIG. 8B illustrates use of a bone graft impactor 200 to introduce graft material 84 such as autologous bone or the like into the disc space 8. The adjacent vertebrae are distracted to provide an intervertebral space having a height slightly less than the height 16 of implant 10 as described above and the initial insertion of the distal end portion of the implant 10 into the disc space 8 is performed in FIG. 8C, while the instrument 100 is in the initial configuration relative to the implant 10. It is noted that the distraction could be performed so that the intervertebral space has a height greater than height 16, but this is not preferred or required.

Figure 8D:
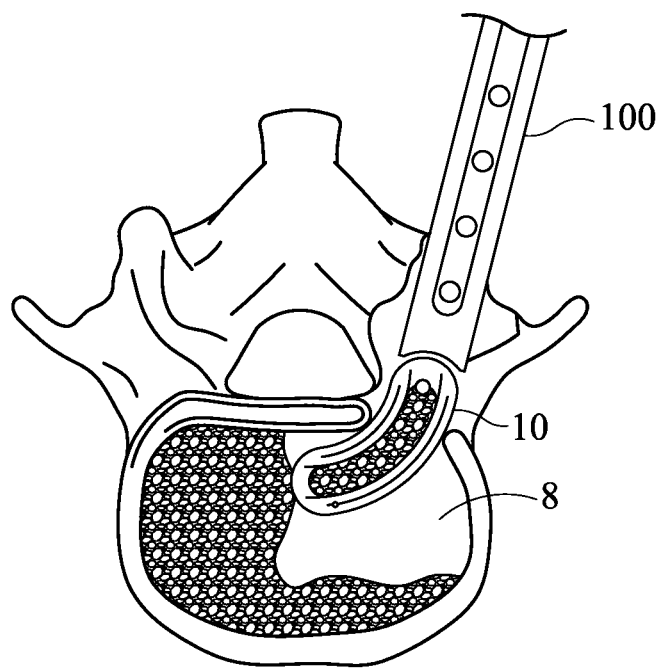

As the implant 10 is advanced further into the disc space and begins to travel along a curved delivery path, the orientation of the implant 10 relative to the instrument 100 can be changed by operating the compression actuator 124 to reduce the compression force sufficiently to unlock the system 1000 and allow pivoting of the implant 10 relative to the instrument 100 until the next adjacent set of facets 52 engage the contact surfaces 108S. The compression actuator 124 can then again be operated to increase the compression force and lock the system down into the locked configuration. FIG. 8D illustrates the implant 10 in the intermediate orientation relative to the instrument 100, where the longitudinal axis L1-L1 now forms a first angle relative to the longitudinal axis L-L and where this angle is the same angle formed between adjacent facets 52.

Figure 8E:
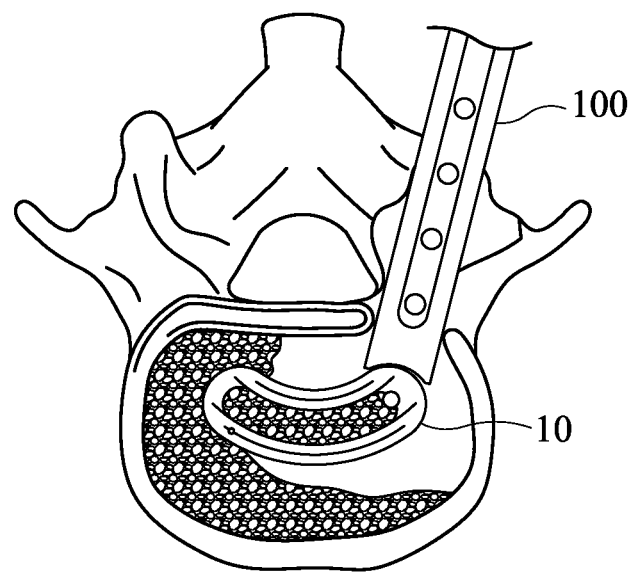
Figure 8F:
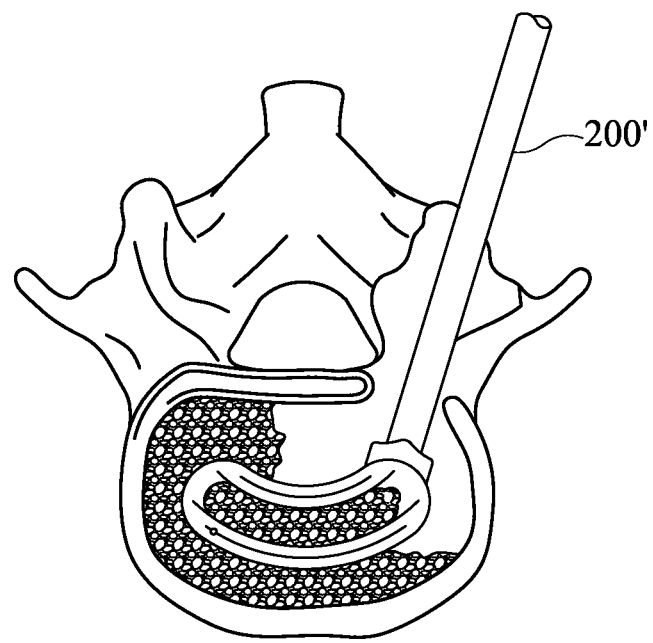

FIG. 8E shows the implant 10 and instrument in the final configuration, in which the axes L-L and L1-L1 now form a second angle equal to two times the angulation between adjacent facet surfaces. At this stage, the implant 10 can be further advanced into ultimate implantation location transverse to the posterior-anterior direction and in the anterior aspect of the disc space 8. At this time, the instrument 100 can be detached from the implant 10 in a manner described above and removed from the patient. Optionally, an impaction tool (impactor 200') may be used in FIG. 8F to drive the implant 10 further into position in amongst the bone ingrowth material 84. Once placement of the implant 10 has been completed to the satisfaction of the surgeon, the remainder of the fusion procedure can be performed according to current techniques.

Since the implants 10 are symmetrical, they can be used for an opposite side approach to that described above by simply flipping the implant 10 over and then performing a procedure as described above, but from the opposite side of the patient.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An interbody implant system comprising:
    an implant including a body have a distal end portion and a proximal end portion and a first articulation surface formed at a proximal end of said proximal end portion; and
    an insertion instrument including an elongate shaft having a proximal end portion and a distal end portion; a second articulation surface formed at a distal end of said distal end portion, said second articulation surface configured to interface with said first articulation surface; and an attachment member configured to connect said implant to said insertion instrument;
    said body of said implant having an elongate opening formed in said proximal end portion, said elongate opening having a first height dimension and a first width dimension, wherein said first height dimension and said first width dimension are not equal;
    said attachment member having a distal attachment portion having a second height dimension and a second width dimension, said second height dimension being unequal to said second width dimension in a plane normal to a longitudinal axis of said attachment member, wherein said second height dimension is less than said first height dimension and said second width dimension is less than said first width dimension, but said second width dimension is greater than said first height dimension;
    wherein said attachment member is actuatable to rotate about a longitudinal axis of said elongate shaft, relative to said elongate shaft, and to compress the first and second articulation surfaces together in a locked configuration with sufficient force to prevent relative rotation between said first and second articulation surfaces, and said attachment member is actuatable to reduce an amount of compression force existing in said locked configuration to place the first and second articulation surfaces in an unlocked configuration such that said first articulation surface can rotate relative to said second articulation surface.

2. The system of claim 1, wherein said second articulation surface is substantially V-shaped.

3. The system of claim 1, wherein said first articulation surface comprises multiple, flat facets adjacent one another.

4. The system of claim 3, wherein said second articulation surface is substantially V-shaped having two contacting surfaces, wherein each of said contacting surfaces contacts one of said facets.

5. The system of claim 4, wherein one of said facets is located between said facets contacted by said contacting surfaces.

6. The system of claim 1, further comprising a connection actuator located on a proximal end portion of said elongate shaft, said connection actuator being actuatable to rotate said attachment member about the longitudinal axis, from a first, unlocked orientation to a second, locked orientation and from said second orientation to said first orientation.

7. The system of claim 1, further comprising a compression actuator located on said proximal end portion of said elongate shaft, said compression actuator being actuatable to move said attachment member in an axial direction relative to said elongate shaft along a longitudinal axis of said elongate shaft.

8. The system of claim 1, wherein said implant comprises first and second curved sides extending between said proximal and distal end portions and top and bottom surfaces formed between proximal and distal ends of said body in a generally lengthwise direction, wherein said top and bottom surfaces each comprise an elongated tooth adjacent each said side, extending generally along the lengthwise direction in which of each respective side extends and protruding outwardly from said respective surface.

9. An interbody implant comprising:
    an implant including a body have a distal end portion and a proximal end portion and a first articulation surface formed at a proximal end of said proximal end portion, wherein said body is unitary and comprises first and second curved sides extending in a generally lengthwise direction between said proximal and distal end portions and top and bottom surfaces bounded by said first and second sides and proximal and distal ends of said body, and at least one elongated tooth adjacent each said side on each of said top and bottom surfaces, each said elongated tooth extending generally along the lengthwise direction in which each respective side extends and protruding outwardly from said respective surface;
    wherein said first articulation surface is configured and dimensioned to interface with a second articulation surface of an insertion instrument having an elongate shaft and said implant is configured and dimensioned to be connected to an attachment member of the insertion instrument, such that the attachment member is actuatable to rotate about a longitudinal axis of said elongate shaft, relative to said elongate shaft, and to compress the first and second articulation surfaces together in a locked configuration with sufficient force to prevent relative rotation between the first and second articulation surfaces, and the attachment member is actuatable to reduce an amount of compression force existing in the locked configuration to place the first and second articulation surfaces in an unlocked configuration such that that first articulation surface can rotate relative to the second articulation surface.

10. The implant of claim 9, wherein said implant comprises an elongate opening configured and dimensioned to allow the attachment member, in a first orientation relative to said elongate opening, to freely pass through said elongate opening, and to prevent passage of the attachment member therethrough when the attachment member is in a second orientation relative to said elongate opening.

11. The implant of claim 9, wherein said implant is unitary.

12. The implant of claim 9, further comprising at least one retropulsion resistor formed in at least one of said at least one elongated tooth, each said retropulsion resistor being configured to permit advancement of said implant into an interbody space, but to prevent retropulsion of said implant out of the interbody space.

13. The implant of claim 9, further comprising at least one series of teeth aligned along a curvature that generally conforms to a curvature of one of said sides.

14. The implant of claim 13, further comprising a series of retropulsion resistors formed in an intermediate section of each of said teeth, respectively, each said series of retropulsion resistors being configured to permit advancement of said implant into an interbody space, but to prevent retropulsion of said implant out of the interbody space.

15. An insertion instrument for inserting an interbody implant, said instrument comprising:
an elongate shaft having a proximal end portion and a distal end portion; an articulation surface formed at a distal end of said distal end portion, said articulation surface configured to interface with an interbody implant articulation surface; and an attachment member configured to connect an interbody implant to said insertion instrument, said attachment member extending distally from said articulation surface of said elongate shaft, said attachment member having a cross-sectional conformation taken transverse to a longitudinal axis of said shaft, said cross-sectional conformation having a height dimension and a width dimension, wherein said height dimension is unequal to said width dimension;
wherein said attachment member is actuatable to rotate about a longitudinal axis of said elongate shaft, relative to said elongate shaft, and to compress the articulation surface of said instrument and the interbody implant articulation surface together in a locked configuration with sufficient force to prevent relative rotation between the articulation surfaces, and said attachment member is actuatable to reduce an amount of compression force existing in said locked configuration to place the articulation surfaces in an unlocked configuration such that said interbody implant articulation surface can rotate relative to said articulation surface of said instrument.

16. The instrument of claim 15, wherein said articulation surface of said instrument is substantially V-shaped.

17. The instrument of claim 15, further comprising a connection actuator located on a proximal end portion of said elongate shaft, said connection actuator being actuatable to rotate said attachment member from a first orientation, unlocked relative to the implant body, to a second, locked orientation, relative to said implant body, and from said second orientation to said first orientation.

18. The instrument of claim 15, wherein said attachment member comprises the shape of a hammer head, said hammerhead being generally oblong having a greater dimension along one axis than a dimension normal to said one axis.

19. The instrument of claim 15, further comprising a compression actuator located on said proximal end portion of said elongate shaft, said compression actuator being actuatable to move said attachment member in an axial direction relative to said elongate shaft along a longitudinal axis of said elongate shaft.

* * * * *

UNITED STATES PATENT AND TRADEMARK OFFICE
CERTIFICATE OF CORRECTION

PATENT NO. : 8,956,414 B2  
APPLICATION NO. : 12/764614  
DATED : February 17, 2015  
INVENTOR(S) : Asaad Page 1 of 1

It is certified that error appears in the above-identified patent and that said Letters Patent is hereby corrected as shown below:

In the Specification  
Column 2, line 23, please delete "f bone" and insert --of bone--;  
Column 4, line 60, please delete "over a least" and insert --over at least--.

Signed and Sealed this  
Fifth Day of July, 2016

Michelle K. Lee  
*Director of the United States Patent and Trademark Office*